(12) United States Patent
Carol (10) Patent No.: US 11,260,249 B2
(45) Date of Patent: Mar. 1, 2022

(54) SYSTEM, APPARATUS AND METHOD FOR HIGH INTENSITY FOCUSED ULTRASOUND AND TISSUE HEALING ACTIVATION

(71) Applicant: SONACARE MEDICAL, LLC, Charlotte, NC (US)

(72) Inventor: Mark Carol, Charlotte, NC (US)

(73) Assignee: Sonablate Corp., Charlotte, NC (US)

( * ) Notice: Subject to any disclaimer, the term of this patent is extended or adjusted under 35 U.S.C. 154(b) by 387 days.

(21) Appl. No.: 16/039,396

(22) Filed: Jul. 19, 2018

(65) Prior Publication Data

US 2020/0023207 A1 Jan. 23, 2020

(51) Int. Cl.
*A61N 7/02* (2006.01)
*C12N 5/071* (2010.01)
(Continued)

(52) U.S. Cl.
CPC .............. *A61N 7/02* (2013.01); *A61B 5/0036* (2018.08); *A61B 8/42* (2013.01); *A61B 8/4494* (2013.01);
(Continued)

(58) Field of Classification Search
CPC ................ A61N 7/02; A61N 2007/025; A61N 2007/0078; C12N 5/068; A61B 5/0036;
(Continued)

(56) References Cited

U.S. PATENT DOCUMENTS 6,685,640 B1 * 2/2004 Fry ........................ A61N 7/022
600/27
7,559,905 B2 7/2009 Kagosaki et al.
(Continued)

FOREIGN PATENT DOCUMENTS

CA 2662997 C 3/2008
CA 2699408 A1 3/2009
(Continued)

OTHER PUBLICATIONS

Burks et al., "Noninvasive Pulsed Focused Ultrasound Allows Spatiotemporal Control of Targeted Homing for Multiple Stem Cell Types in Murine Skeletal Muscle and the Magnitude of Cell Homing Can Be Increased Through Repeated Applications", Stem Cells, vol. 31, pp. 2551-2560 (2013).
(Continued)

*Primary Examiner* — Joseph M Santos Rodriguez
*Assistant Examiner* — Zainab Mohammed Aldarraji
(74) *Attorney, Agent, or Firm* — Mark T. Vogelbacker; Eckert Seamans Cherin & Mellott LLC (57) ABSTRACT

A method of treating colorectal cancer included placing a high intensity focused ultrasound (HIFU) probe proximate a designated treatment volume at one of the colon and the rectum of a patient. The method further includes delivering HIFU via the HIFU probe at a frequency of at least 1 mHz for at least 3 seconds to raise a temperature of a first portion of the designated treatment volume to above 65° C., thereby ablating the first portion and causing a tissue defect within the designated treatment volume. The method further includes applying a nonablative dose of energy via the HIFU probe to a second portion of the designated treatment volume to provoke stem cell homing in the second portion, thereby encouraging tissue regrowth.

11 Claims, 6 Drawing Sheets

(51) Int. Cl.
*A61B 5/00* (2006.01)
*A61B 8/00* (2006.01)
*A61B 8/08* (2006.01)

(52) U.S. Cl.
CPC ............ *A61B 8/5207* (2013.01); *C12N 5/068* (2013.01); *A61N 2007/025* (2013.01)

(58) Field of Classification Search
CPC ....... A61B 8/4494; A61B 8/42; A61B 8/5207; A61B 8/08; A61B 2017/00154; A61B 34/25; A61B 2090/3762; A61B 2090/374
See application file for complete search history.

(56) References Cited

U.S. PATENT DOCUMENTS

| | | | |
|---|---|---|---|
| 7,662,114 B2 | 2/2010 | Seip et al. | |
| 8,038,631 B1 | 10/2011 | Sanghvi et al. | |
| 8,162,858 B2 | 4/2012 | Manna | |
| 8,235,902 B2 | 8/2012 | Chen et al. | |
| 9,011,336 B2* | 4/2015 | Slayton | A61N 7/00 600/439 |
| 9,095,695 B2 | 8/2015 | Fedewa et al. | |
| 9,409,041 B2 | 8/2016 | Fedewa et al. | |
| 9,452,302 B2* | 9/2016 | Slayton | A61N 7/02 |
| 9,457,202 B2 | 10/2016 | Sanghvi et al. | |
| 9,827,449 B2* | 11/2017 | Barthe | A61B 8/08 |
| 9,974,983 B2 | 5/2018 | Carol | |
| 10,183,182 B2* | 1/2019 | Slayton | A61B 8/5246 |
| 10,772,681 B2* | 9/2020 | Gertner | A61B 18/1492 |
| 10,849,679 B2* | 12/2020 | Anand | A61B 18/1492 |
| 2005/0038340 A1* | 2/2005 | Vaezy | A61B 8/0833 600/439 |
| 2009/0230822 A1 | 9/2009 | Kushculey et al. | |
| 2010/0092424 A1* | 4/2010 | Sanghvi | A61B 8/0833 424/85.2 |
| 2010/0241005 A1* | 9/2010 | Darlington | A61N 7/02 600/459 |
| 2011/0144490 A1* | 6/2011 | Davis | A61N 7/02 600/439 |
| 2011/0144545 A1* | 6/2011 | Fan | A61N 7/02 601/3 |
| 2014/0243677 A1 | 8/2014 | Johnson et al. | |
| 2014/0277035 A1 | 9/2014 | Strait et al. | |
| 2014/0330124 A1* | 11/2014 | Carol | A61B 8/12 600/439 |
| 2014/0330175 A1 | 11/2014 | Carol | |
| 2014/0378832 A1 | 12/2014 | Sanghvi et al. | |
| 2015/0265365 A1* | 9/2015 | Andrews | A61F 5/3707 600/411 |
| 2015/0321027 A1 | 11/2015 | Fedewa et al. | |
| 2016/0166855 A1* | 6/2016 | Kumar | A61N 5/1039 600/1 |
| 2016/0220302 A1* | 8/2016 | Zarins | A61B 8/12 |
| 2016/0235484 A1 | 8/2016 | Carol | |
| 2016/0236013 A1 | 8/2016 | Carol | |
| 2016/0332005 A1 | 11/2016 | Fedewa et al. | |
| 2017/0014651 A1* | 1/2017 | Sanghvi | A61P 43/00 |
| 2017/0203131 A1* | 7/2017 | Carol | A61B 8/4444 |
| 2017/0312021 A1* | 11/2017 | Pilcher | A61N 1/36002 |
| 2017/0319875 A1 | 11/2017 | Carol et al. | |
| 2018/0085606 A1 | 3/2018 | Seip et al. | |
| 2018/0161001 A1 | 6/2018 | Seip et al. | |
| 2018/0161603 A1 | 6/2018 | Seip et al. | |
| 2018/0161604 A1 | 6/2018 | Chaluisan et al. | |
| 2018/0214612 A1* | 8/2018 | Dai | A61L 27/24 |
| 2020/0023207 A1* | 1/2020 | Carol | A61B 34/25 |

FOREIGN PATENT DOCUMENTS

| | | | |
|---|---|---|---|
| CA | 2706563 A1 | 6/2009 | |
| CN | 106061401 A | 10/2016 | |
| EP | 2207596 B1 | 5/2013 | |
| EP | 1755458 B1 | 2/2015 | |
| EP | 2069018 B1 | 7/2016 | |
| EP | 3054858 | 8/2016 | |
| EP | 3055027 | 8/2016 | |
| EP | 3108934 A1 | 12/2016 | |
| JP | 5064386 B2 | 8/2012 | |
| JP | 5462167 B2 | 1/2014 | |
| JP | 5615548 B2 | 10/2014 | |
| JP | 6046094 B2 | 11/2016 | |
| JP | 2016533784 A | 11/2016 | |
| JP | 2016538014 A | 12/2016 | |
| KR | 20160068922 A | 6/2016 | |
| WO | 2015054592 A1 | 4/2015 | |
| WO | 2015054605 A1 | 4/2015 | |
| WO | WO-2016196741 A2 * | 12/2016 | ............... A61N 7/02 |
| WO | 2017083133 A1 | 5/2017 | |
| WO | 2017127383 A1 | 7/2017 | |

OTHER PUBLICATIONS

Written Opinion issued in PCT/US2017/013853, dated Mar. 31, 2017.

International Search Report issued in PCT/US2017/013853, dated Mar. 31, 2017.

International Preliminary Report of Patentability issued in PCT/US2017/013853, dated Apr. 12, 2018.

* cited by examiner

SYSTEM, APPARATUS AND METHOD FOR HIGH INTENSITY FOCUSED ULTRASOUND AND TISSUE HEALING ACTIVATION

SUMMARY

Ultrasound waves can be focused onto very small volumes of tissue, which increases greatly their intensity; hence the name high intensity focused ultrasound (HIFU). Focused beams can be created using spherically-curved transducers or by other means (using phased arrays, for example), allowing energy to be deposited deep inside the body. The ultrasound waves can pass through the skin and/or other intervening tissues over a wide area producing relative low spatial intensities and consequently create no or very little damage until the waves coalesce at the focus, where intensities can be 3 to 4 orders of magnitude higher than at the transducer surface.

Ablative HIFU delivers energy using frequencies ranging from approximately 1-5 MHz or higher with a beam on duration of anywhere from approximately 1-60 seconds at a time. By focusing the acoustic energy inside a tumor, HIFU rapidly can raise the tissue temperature at its beam focus well above 65° C., leading to thermal lesion formation and/or cellular coagulative necrosis and in a well-defined region. Coagulative necrosis can be characterized by the formation of a gelatinous substance in dead tissues in which the tissue is maintained and can be observed by light microscopy. Coagulation occurs as a result of protein denaturation that causes the albumin in proteins to form a firm and opaque state.

All tissue whose temperature rises above 60-65° C. for three seconds, normal or cancerous, is killed. HIFU presently is being used to ablate tumors noninvasively, where relatively long, continuous exposures are employed to produce the required high temperature elevations for thermal ablation and direct tumor destruction.

While ideal for destroying solid tumors, ablative HIFU is generally not an ideal where normal and cancer cells are intermingled or in close proximity, and where it is desirous to preserve the normal cells. Such scenarios occur at the periphery of a solid tumor or in micro-metastatic disease found distant from the primary tumor site. The physician must determine whether to ablate all cancer along with some normal tissue, or to preserve all normal tissue along with some cancer cells.

HIFU can be used to impact cancers in several other ways other than just pure ablation. A number of preclinical studies have evaluated the potential of combining HIFU ablation exposures with chemotherapy for the treatment of tumors. These include the use of doxorubicin in liver tumors, adriamycin in neuroblastoma, fluorouracil in peritoneal carcinomatosis, and paclitaxel and estramustine in an AT2 Dunning adenocarcinoma. It is generally thought that the improved effects of combining HIFU and these agents occurs outside of the immediate treatment zone of the HIFU beam (i.e., where thermal cytotoxicity is not occurring) and is due either to the agents sensitizing the cells to increase the normally subtherapeutic effects of the HIFU exposures, or conversely, to the sub-lethal HIFU effects that improve the uptake of the agents.

HIFU also has been shown to enhance the activity of other approaches to treating cancer such as immunotherapy. The induction and maintenance of an effective antitumor immune response can be dependent critically on dendritic cells (DCs) functioning as antigen-presenting cells (APCs). Dendritic cells can capture antigens in peripheral tumor tissues and migrate to secondary lymphoid organs, where they cross-present the captured antigens to T cells and activate them. To act as potent APCs, DCs must undergo maturation, a state characterized by the upregulation of major histocompatibility complex (MHC) and costimulatory molecules and the production of cytokines such as IL-12. However, the requisite signals for DC maturation are often absent from the bed of poorly immunogenic tumors. Preliminary evidence from several recent clinical and experimental studies has suggested that HIFU may be unique among the various means of thermal energy delivery in its ability to enhance host systemic anti-tumor immunity by stimulating the release of endogenous immunostimulatory factors from tumor cells that encourage DCs to mature.

As has been observed with pharmaceuticals, infiltrated DCs are recruited mostly to the periphery of thermal lesions after HIFU exposure and tumor cells at the periphery of HIFU-induced thermal lesions are most effective at stimulating DCs to mature. The periphery of a thermal lesion is a region that experiences a reversible heat effect on cells; the dose of heat is not sufficient to destroy irreversibly the cells but is perhaps sufficient to produce transient reversible changes to cell membrane and cytoplasmic function. Studies of other forms of focused ultrasound that are designed specifically to have only a reversible component to their tissue interaction (sometimes called low intensity focused ultrasound or pulsed high intensity focused ultrasound) have shown that changes in membrane permeability and other cellular function may allow cellular components to become more "visible" to blood borne cells, cellular components and, presumably, to circulating drugs.

In order for any of these blood-borne agents to produce an effect on targeted cells, either with or without combination with focused ultrasound, the agents need to get to the targeted volume. Unfortunately, a number of factors have been identified in the microenvironment of solid tumors that are responsible for non-uniform and insufficient levels of anti-cancer agents being delivered to the cancerous tissue. These occur due to abnormalities in both the vasculature and the extracellular matrix that lead to deficiencies in transvascular and interstitial transport, respectively, and that can effect ultimately the bioavailability and efficacy of chemotherapeutic agents.

Compared to normal tissues, blood vessels in tumors are leaky, possessing large gaps between endothelial cells. The vasculature is also chaotic in regards to spatial distribution, microvessel length and diameter, and can be tortuous and saccular and possess haphazard interconnections that render the vessels functionally abnormal. Proliferating tumor cells can also generate solid pressure on blood vessels that will further impair blood flow. Another important characteristic of the tumor microenvironment is that the combination of a leaky vasculature and a lack of functional lymphatics can create increased interstitial fluid pressures found just past the periphery of solid tumors. As a result, extravasation of large convection-dependent agents can be severely limited.

Another often overlooked factor for insufficient delivery of anti-cancer agents to tumor cells is the increase in mean distance between tumor cells and the blood vessels that they supply. Whereas the well-organized, normal tissues of the human body enable most cells to be within a few cell diameters of a blood vessel, this is often not the case in solid tumors. Relatively higher cell proliferation rates in tumors, compared to normal tissues, can result in tumor cells forcing vessels apart, leading to a reduction in vascular density. As a result, populations of cells are created that can be more than 100 μm from blood vessels, a problem that may be exacerbated further by the already poor organization of the tumor vasculature. This phenomenon can lead to limited access of drugs to tumor cells distant from blood vessels.

The distance between the tumor cells and the vessels can also reduce the delivery of oxygen to the cancer cells thereby creating conditions of hypoxia. It is well known that cancers begin to become hypoxic in their interior when they reach approximately 1 $cm^3$ in volume (1 cm in diameter). Tumor hypoxia can lead to overexpression of HIF-1a, which signals the production of CD24, which helps tumors grow and metastasize. In addition to aggression, CD24 has also been shown to confer resistance to the tumor cells against most chemotherapy, allowing this small population of resistant cells to regrow the tumor once chemotherapy ends, leading to relapse and disease progression. Furthermore, regions of tumor that are under vascularized and hypoxic can be subject to the build-up of metabolic products (e.g., carbonic and lactic acid) that lower the extracellular pH and affect the cellular uptake of some drugs.

Thus, specific cancer cells situated within a volume of cancer cells cannot be expected to be destroyed by approaches that require normal vascularization, such as chemotherapy or an immune system response requiring dendritic cells and T-cells being delivered to the cancer cells.

In summary, the tumor microenvironment poses a formidable obstacle to enabling uniform and adequate delivery of anticancer agents. If delivered successfully, anticancer agents could substantially improve the treatment of solid tumors. Considerable effort, therefore, has gone into finding ways to modify the tumor microenvironment for this purpose with limited success.

A potential approach is to use ablation to control the primary solid cancer and to use a secondary means, such as an immunomodulatory agent, to control microscopic and metastatic disease. Unfortunately, this approach has its drawbacks as well. In clinical practice a HIFU treatment targets typically the entire cancer volume, ablating all cancer cells. Since the region of heat falloff occurs where there are normal cells, there is an insufficient volume of cancer cells that receive a reversible dose of HIFU to result in immune system stimulation. It, therefore, is reasonable to speculate that an optimized HIFU strategy that can increase the effectiveness of anti-tumor agents at the periphery of a tumor and/or locations of metastatic activity, yet still ablate solid portions of a cancer, would be desirable.

One possible approach is a staged treatment: a dose of heat is delivered to the entire target volume in order to stimulate the immune system and then, at some later time, a lethal dose of heat is delivered to the same target volume. This approach has the benefit of eliciting potential immune system stimulation from the largest volume of tumor possible and a response that targets all clones of cancer cells within the zone of treatment. However, it gives the primary target volume longer to grow in an untreated environment and it requires multiple visits on the part of the patient to the treating facility.

An alternative approach has been proposed in the prior art that requires only a single visit. Labelled "sparse-scan" strategy, it creates discrete HIFU lesions within the targeted volume of cancer cells that are separated by viable cancer tissue between the lesions. The goal of this approach is to ablate zones of solid cancer while preserving reversibly impacted surrounding regions of tumor tissue that may provide stimuli for DC maturation, thereby enhancing the strength of HIFU-induced systemic antitumor immune response.

While this approach may produce an enhanced antitumor immune response that might be effective against micrometastatic disease throughout the patient, it can be problematic as a means of controlling the primary disease itself. Part and parcel of the sparse-scan approach is the preservation of cancer cells in the interior of a cancer volume. A sparse scan strategy leaves viable tissue within the interior of a tumor that is to be destroyed by vascular delivery of dendritic cells and activated T-cells, yet for which there is limited or no vascular supply.

Another possible approach is through the use of shorter pulses of HIFU given in combination with relatively short duty cycles, resulting in a decrease in the temporal average intensities of the HIFU dose. Rather than the continuous high frequency acoustic energy used with ablative doses of HIFU, pulsed focused ultrasound (pFUS) uses a lower frequency (100 KHz-1 MHz) delivered in bursts as short as 1-10 milliseconds at a time. This reduces the generation of heat resulting in non-lethal temperature elevations in the targeted tissue. Such exposures, which generate transient temperature elevations of only approximately 4° C. to 5° C., have been used to noninvasively enhance local delivery of various macromolecules into different tissue types, improving their therapeutic effects. Since the pulsed dose is not sufficient to ablate the solid portion of the tumor, additional technology would be required to provide the ablative dose of focused ultrasound to be used in conjunction with the reversible dose.

Therefore, an improved way would be beneficial to provide enhanced activation of the immune system, in order to destroy cancer cells that cannot be targeted directly by HIFU, while at the same time destroying all cancer cells with targeted HIFU that cannot be impacted by an enhanced immune system response.

In one embodiment, the present disclosure includes a means for delivering an ablative dose of focused ultrasound that will spare purposefully some portion of a volume of cancer cells targeted for ablation, where that portion can be sufficient to elicit an enhanced immune system response. A HIFU probe can be provided, with or without on-board imaging, capable of delivering or configured to deliver an ablative dose of energy to a designated treatment volume. Algorithms can be provided for determining a volume of cancer cells, typically at the periphery of the targeted volume and sufficient to elicit an enhanced immune system response, and for adjusting the volume of ablation to result in the sparing of that volume of cancer cells. Signal interrogation and processing algorithms can be provided to assess temperature inside the region of ablation and in the region of dose falloff in order to insure that the designated tissue is ablated while the region targeted for sublethal dosing receives such a sublethal thermal dose.

In a further embodiment, the present disclosure includes a means for delivering an ablative dose of focused ultrasound to a designated volume of cancer cells and a nonlethal dose of focused ultrasound to a second designated volume of cancer cells. A HIFU probe can be provided, with or without on-board imaging, capable of delivering or configured to deliver an ablative dose of energy using at least one pulse sequence and set of parameters designed to achieve such, and also is capable of delivering or configured to deliver a nonlethal dose of energy using at least one distinctly different pulse sequence and set of parameters designed to achieve such a nonlethal dose. Algorithms can be provided for determining a volume of cancer cells, typically at the periphery of the targeted volume and sufficient to elicit an enhanced immune system response, and for adjusting the volume of ablation to result in the sparing of that volume of cancer cells. Signal interrogation and processing algorithms can be provided to assess temperature inside the region of ablation and in the region of dose falloff in order to ensure that the designated tissue is ablated while the region targeted for sublethal dosing receives such a sublethal thermal dose.

In one embodiment, the present disclosure includes a method for delivering an ablative dose of focused ultrasound that will spare purposefully some portion of a volume of cancer cells targeted for ablation, wherein that portion can be sufficient to elicit an enhanced immune system response. The method can include the placement of a HIFU probe, with or without on-board imaging, adjacent to or within the designated treatment volume; the determination of the volume of cancer cells, typically at the periphery of the targeted volume, sufficient to elicit an enhanced immune system response; a reduction in the designated treatment volume by the volume of cancer cells sufficient to elicit an enhanced immune system response; the ablation of the adjusted designated treatment volume; the use of signal interrogation and processing algorithms to assess the temperature inside the region of ablation and also in the region of dose falloff; whereby the designated tissue can be ablated while the volume required to produce an enhanced immune system response receives only a sublethal thermal dose.

In one embodiment, the present disclosure includes a further method for delivering an ablative dose of focused ultrasound that will spare purposefully some portion of a volume of cancer cells targeted for ablation, where that portion can be sufficient to elicit an enhanced immune system response. The method can include the placement of a HIFU probe, with or without on-board imaging, adjacent to or within the designated treatment volume; the ablation of the designated treatment volume using at least one pulse sequence and set of parameters designed to achieve such an ablation; the use of the same probe to deliver, without adjusting the position of the probe, a nonlethal nonablative dose of energy to a second volume of tissue using at least one distinctly different pulse sequence and set of parameters designed to achieve such a nonlethal dose; the use of signal interrogation and processing algorithms to assess the temperature inside the region of ablation and also in the region of sublethal damage; whereby a designated volume of tissue can be ablated while a second volume of tissue can receive a sublethal dosing of energy sufficient to elicit an immune system response.

HIFU can be used in situations where a nonablative impact is desired. Shorter pulses of HIFU given in combination with relatively short duty cycles will result in a decrease in the temporal average intensities of the HIFU dose. Rather than the continuous high frequency acoustic energy used with ablative doses of HIFU, pFUS or nonablative focused ultrasound (NAFUS) uses a lower frequency (100 KHz -1 MHz) delivered in bursts as short as 1-10 milliseconds at a time. As described above, this reduces the generation of heat resulting in non-lethal temperature elevations in the targeted tissue. Such exposures, which generate transient temperature elevations of only 4° C. to 5° C., have been used to enhance noninvasively local delivery of various macromolecules to different tissue types, improving their therapeutic effects.

One clinical indication being explored for ablative HIFU is in the treatment of rectal cancer. Approximately 40-60% of cancers falling under the designation "colorectal cancer" are rectal in location, and approximately 40-60% of these are considered early stage, localized to a portion of the rectal wall that can be identified using advanced imaging techniques and that can be reached by a transrectal probe. "Colorectal cancer" is defined herein as a cancer that starts in the colon or the rectum. These cancers can also be named colon cancer or rectal cancer, depending on where they originate.

The current standard of care for early stage rectal cancer is surgical resection of the malignancy. This can be via local resection (T1 disease) or total mesorectal excision (TME). 40% of rectal cancers are local and amendable to these limited surgical approaches, resulting in a 90+% five year survival. However, primary resection for early stage disease is not without its drawbacks. Even with the widespread use of laparoscopic resections, many patients are left with significant morbidity following the life altering surgery. The operative morbidity can be considerable particularly if an open operation is required. There is also significant risk of long term functional pathology post resection that has considerable impact on quality of life. Anterior resection syndrome affects up to 70% of patients post TME, with these patients having worse quality of life scores than patients who are not affected. While the pathophysiology is not yet fully understood, it does represent a significant burden of morbidity for these patients with no effective treatment. This highlights the need for alternative/additional treatment options in all stages rectal cancer to improve outcome and reduce morbidity.

HIFU has been and is being used commonly for the transrectal ablation of prostate cancer. Short and medium-term data demonstrate that HIFU may be equivalent to some current prostate cancer therapies but with reduced morbidity and length of stay. As the prostate and rectum are adjacent, there is now a natural evolution to translate the success in prostate to the adjacent rectum/other pelvic structures. One such application is in the treatment of local rectal cancer, where the tumor and a surrounding margin are ablated directly.

One of the potential risks associated with the use of ablative energies, such as HIFU, in the local treatment of rectal cancer is penetration of the rectal wall or the creation of a rectal fistula due to full thickness rectal wall thermal injury.

Stem cells have been shown to be effective in encouraging tissue regrowth required to close rectal fistulas or other tissue defects. Fistulas can occur spontaneously due to Crohn's disease or following surgery for rectal cancer. Unfortunately, it can be difficult to get stem cells to the region of tissue defect and/or confine them or to get them to "stay in the region of interest."

NAFUS and pFUS have a beneficial effect on the ability of stem cells (SC) to implement change. One of the main obstacles to the successful treatment with stem cells is getting the stem cells to where they are needed (i.e., stem cell migration or cell homing, which can, for example, include stem cell engraftment and stem cell repopulation) and creating a suitable microenvironment for the stem cells to differentiate into the desired cell lineages. Burks et al., "Noninvasive Pulsed Focused Ultrasound Allows Spatiotemporal Control of Targeted Homing for Multiple Stem Cell Types in Murine Skeletal Muscle and the Magnitude of Cell Homing Can Be Increased Through Repeated Application," STEM CELLS 2013;31:2551-2560, which is hereby incorporated by reference, has shown that NAFUS can be used to target and maximize stem cell delivery by stimulating chemoattractant expression in pFUS-treated tissue prior to cell infusions.

Due to the drawbacks of the prior art, a better way is desired to treat localized rectal cancers while at the same time minimizing the risks associated with potential penetration of the rectal wall (and/or other tissue or organs) during such treatments.

In one embodiment, the presently disclosed technology includes a means for delivering an ablative dose of focused ultrasound to destroy cancerous tissue and simultaneously or sequentially delivering a nonablative dose of HIFU to surrounding or adjacent tissue that will enhance and/or stimulate stem cell homing to repair any tissue defect that may result from the ablative dose. A HIFU probe is provided, with or without on-board imaging, capable of delivering an ablative dose of energy to a designated treatment volume. Signal interrogation and processing algorithms are provided to assess temperature inside the region of ablation and in the region of dose falloff in order to insure that the designated tissue is ablated while the region targeted for sublethal dosing receives a sublethal thermal dose.

In another embodiment, the presently disclosed technology includes a means for delivering an ablative dose of focused ultrasound to a designated volume of cancer cells and a nonlethal dose of focused ultrasound to a second designated volume of surrounding tissue. A HIFU probe is provided, with or without on-board imaging, capable of delivering an ablative dose of energy using at least one pulse sequence and set of parameters designed to achieve such, and also is capable of delivering a nonlethal dose of energy using at least one distinctly different pulse sequence and set of parameters designed to achieve such a nonlethal dose. Signal interrogation and processing algorithms are provided to assess temperature inside the region of ablation and in the region of dose falloff in order to ensure that the designated tissue is ablated while the region targeted for sublethal dosing receives such a sublethal thermal dose.

As is to be appreciated by one skilled in the art, one or more aspects of the foregoing disclosed systems and/or methods may be combined or even omitted, if desirable.

DRAWINGS

The foregoing summary, as well as the following detailed description of the presently disclosed technology, will be better understood when read in conjunction with the appended drawing(s). For the purpose of illustrating the presently disclosed technology, there are shown in the drawings various illustrative embodiments. It should be understood, however, that the presently disclosed technology is not limited to the precise arrangements and instrumentalities shown.

DETAILED DESCRIPTION

Various embodiments of the present disclosure are described hereinafter with reference to the figures. It should be noted that the figures are not drawn to scale and elements of similar structures or functions are represented by like reference numerals throughout the figures. It should also be noted that the figures are not intended to facilitate the description of specific embodiments of the presently disclosed technology. The figures are not intended as an exhaustive description of the invention or as a limitation on the scope of the presently disclosed technology. In addition, an aspect described in conjunction with a particular embodiment of the presently disclosed technology is not necessarily limited to that embodiment and can be practiced in any other embodiments of the presently disclosed technology. Thus, features of any one embodiment disclosed herein can be omitted or incorporated into another embodiment.

It will be appreciated that while various embodiments of the presently disclosed technology are described in connection with radiation treatment of tumors, the claimed invention has application in other industries and to targets other than cancers. Unless specifically set forth herein, the terms "a," "an" and "the" are not limited to one element, but instead should be read as "at least one." Any headings used herein are for organizational purposes only and are not meant to limit the scope of the description or the claims.

Figure 2:
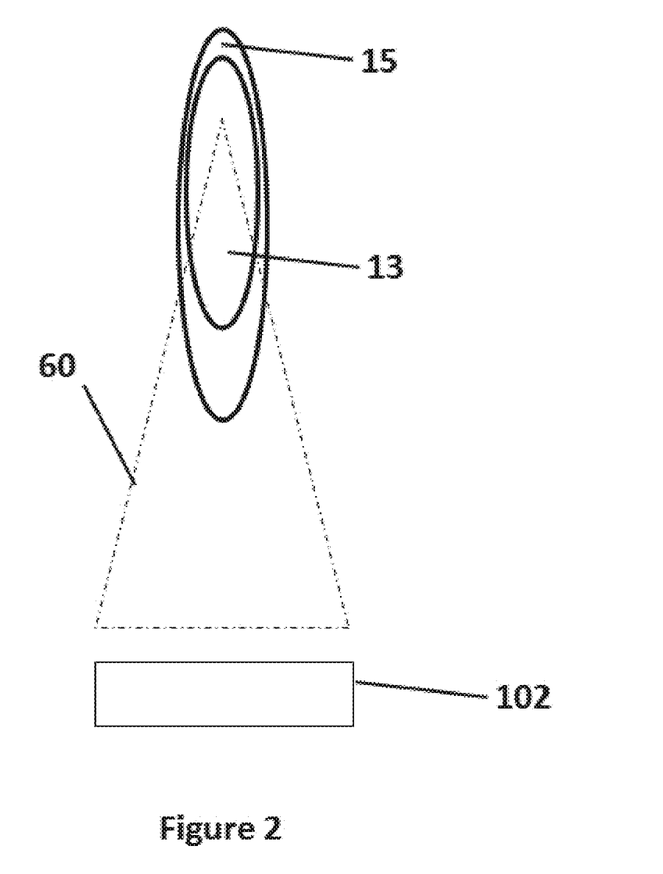
FIG. 2 is a schematic representation of the operation of a probe of one embodiment of the present disclosure.

In one embodiment, the present disclosure includes a system for performing a surgical procedure. The system can include a probe 100 having a shaft 101 and at least one transducer 102 configured to deliver thermal energy to tissue, generally designated 10, to a designated first treatment volume or region, generally designated 12, and/or to a second treatment volume or region, generally designated 14. The first treatment volume 12 can represent a volume for immune activation, stem cell homing, and/or an outer periphery of an ablation zone 13. As shown in FIG. 2, a nonablative or nonlethal region 15 can surround the ablation zone 13. In other words, the nonlethal region 15 can be formed between an outer periphery of the first treatment volume 12 and an inner periphery of the second treatment volume 14.

Figure 3A:
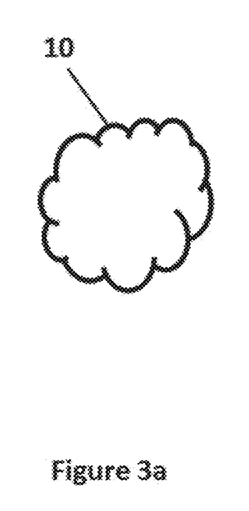
FIG. 3a is a schematic representation of tissue designed to be treated with a probe of one embodiment of the present disclosure.
Figure 3B:
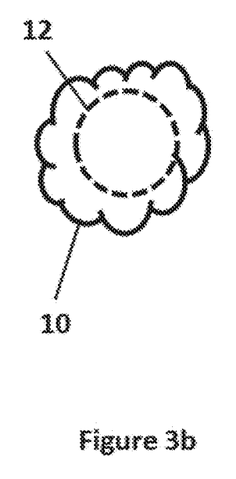
FIG. 3b is a schematic representation of a first treatment volume identified by a system of the present disclosure.
Figure 3C:
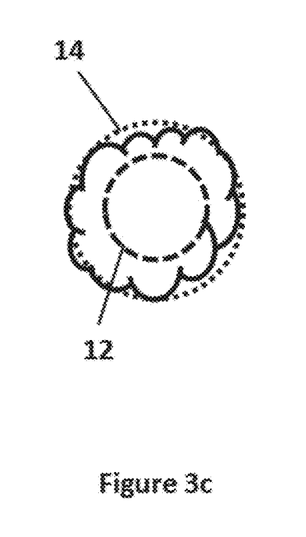
FIG. 3c is a schematic representation of first and second treatment volumes identified by a system of the present disclosure.
Figure 4A:
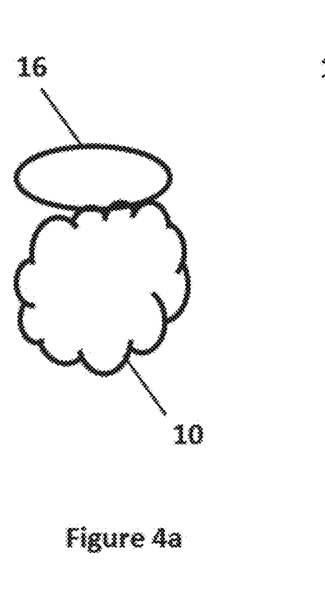
FIG. 4a is a schematic representation of one environment in which a probe of the present disclosure is configured to operate.
Figure 4B:
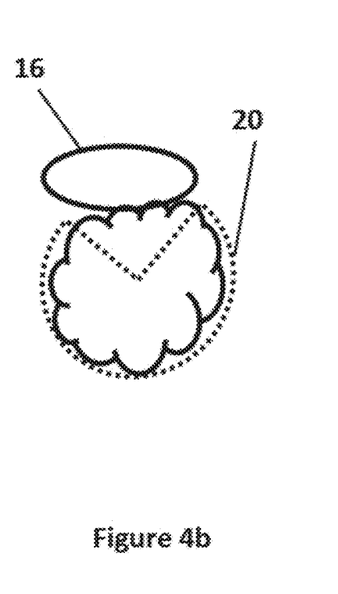
FIG. 4b is a schematic representation of the operation of a probe of one embodiment of the present disclosure.
Figure 4C:
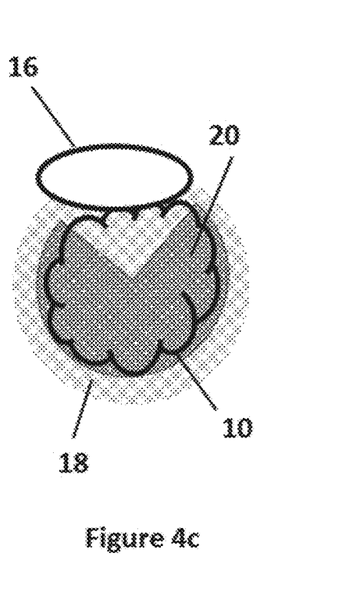
FIG. 4c is a schematic representation of the operation of a probe of one embodiment of the present disclosure.
Figure 5A:
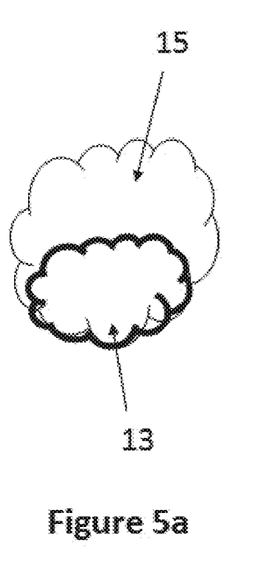
FIG. 5a is a schematic representation of the operation of a probe of one embodiment of the present disclosure.
Figure 5B:
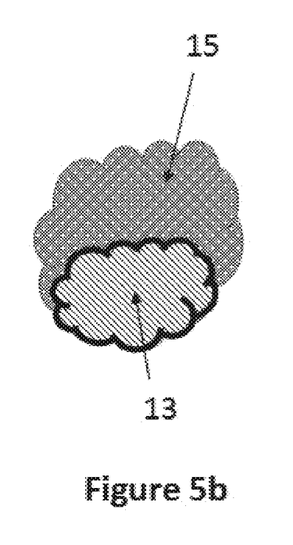
FIG. 5b is a schematic representation of the operation of a probe of one embodiment of the present disclosure.

The transducer can be configured to also generate images of the designated treatment volume and surrounding tissue. The images can be used to correctly position the delivery of thermal energy. A user input interface or display can be provided to define the first treatment volume 12. The user interface can also allow for the designation of the second treatment region 14, volume, or location of tissue, for example at a periphery of the first treatment volume 12 or spaced outwardly from the first treatment volume 12, which can receive a nonablative or sublethal dose of thermal energy (FIG. 4c, for example). Once the second region 14 slated to receive a nonlethal dose has been defined, the settings for delivering the ablative dose of thermal energy to the first volume 12 can be determined such that the dose falloff region of the ablative dose covers the second volume 14 insuring that the second volume receives a sublethal thermal dose. The size, shape, location, and/or configuration of each of the first and second regions 12, 14 can vary depending upon the desired treatment. For example, as shown in FIG. 3c, each region 12, 14 can be generally circular and the regions 12, 14 can be concentric. Alternatively, the first region 12 can have a first shape, while the second region 14 can have a different second shape.

In addition to being related to the size of the ablation volume, the magnitude of the volume of tissue that needs to be exposed to a sublethal dose of thermal energy may be related to cancer type, organ location, and/or other factors impacting the reliability of immune system activation and/or stem cell homing, or it can be determined arbitrarily. The user interface of the probe 100 can provide a means for allowing these factors to be taken into account by entering any combination of the volume of tissue to be exposed to a sublethal dose, the thickness of the rim of tissue surrounding the zone to be ablated that is to be exposed to a sublethal dose, and/or other means that will allow the volume of tissue that is to be exposed to a sublethal dose to be inputted or defined. The presence of critical structures, generally designated 16, (e.g., an organ) (e.g., see FIGS. 4a-4c) close to the target volume can also be considered during the definition of the lethal/sublethal volumes. For example, target volumes close to critical structure(s) can receive a sublethal dose 18, while target volumes further away from the critical structures may be chosen to receive a lethal dose 20 (FIGS. 4b and 4c).

Furthermore, settings used to produce a desired volume of ablation can take into account the dynamics of energy buildup and energy falloff in ablated tissue. With a dose of HIFU sufficient to ablate tissue, the fall-off in thermal energy from ablated to non-ablated tissue can be very sharp in the lateral direction, on the order of a small number of cells. In the direction of the HIFU beam 60 (proximal and distal) (see FIG. 2), the transition zone between ablation and non-ablation is wider. Post-focal (distal) falloff can be fairly steep, comprising a region of dose bleed over from a degree of fuzziness that results from the way the beam is focused onto a relatively small zone, a degree that is relatively independent of the amount of dose delivered to the tissue. Pre-focal (proximal) demarcation between ablation and nonablation is variable and depends to a large degree on the size of the zone of ablation and speed with which energy is deposited in the tissue. In one embodiment, these factors should be taken into account in order to determine the size of the transition zone that will result from a given ablation zone. By knowing the volume of tissue that needs to receive a sublethal dose, and the size of the zone that under ideal circumstances would be ablated, it is possible to determine the volume of ablation that can be realized while still achieving the sublethal volume requirement. An optimization algorithm, such as simulated annealing, combinatorial optimization, dynamic programming, evolutionary algorithm, gradient method, stochastic optimization, and others known to those skilled in the art, may be used to determine the optimal volume of ablation, based on inputted values and tissue characteristics, such that said volume is maximized while still preserving the volume of treated tissue receiving a sublethal thermal dose.

In an alternative embodiment, the region of tissue slated to receive a sublethal dose can be treated with energy delivery parameters different from those used to deliver a lethal or ablative dose. As an example, the parameters for pFUS, which is nonablative, differ greatly from those of ablative focused ultrasound and are designed to ensure that the tissue exposed to pFUS is not ablated. A typical set of parameters for delivering an ablative dose of focused ultrasound include a frequency of approximately 4 MHz versus a pFUS frequency of approximately 1 MHz; a spatial average temporal average intensity ($I_{SATA}$) of approximately 2,500 watts W/cm$^2$ for an ablative dose compared to approximately 100-1,000 W/cm$^2$ for pFUS; and a duty cycle for ablation consisting of several seconds of beam ON time followed by several seconds of beam OFF time (such as 3 sec on/3 sec off; 3 sec on/6 sec off; 3 sec ON/3 sec ON, 3 seconds OFF; etc.) versus a duty cycle of 100 ms ON/900 ms OFF for pFUS. While parameters such as frequency, intensity, and duty cycle are achievable by changing software settings driving a transducer, changing frequency typically requires the use of separate crystals for each frequency, but can also be accomplished by operating the crystal at its 3rd harmonic, for example.

Figure 1A:
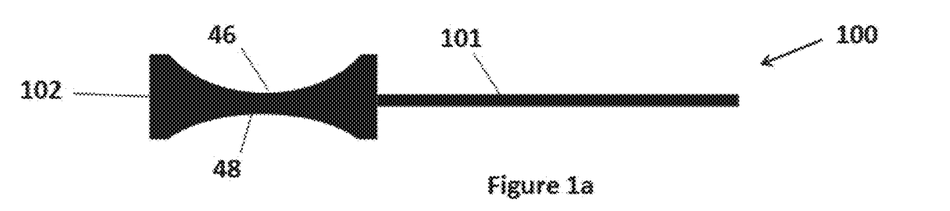
FIG. 1a is a schematic representation of a side elevation view of a probe according to one embodiment of the present disclosure.
Figure 1B:
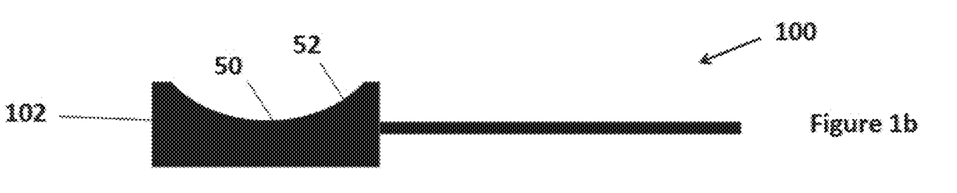
FIG. 1b is a schematic representation of a side elevation view of a probe according to another embodiment of the present disclosure
Figure 1C:
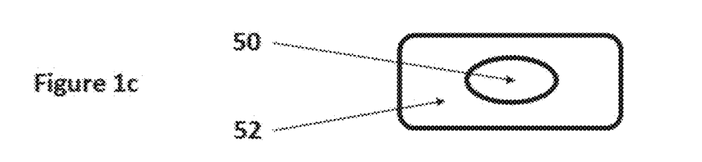
FIG. 1c is a schematic representation of a top plan view of a portion of the probe of FIG. 1b.

Referring to FIGS. 1a-2, the probe 100 can be provided equipped with one or more ultrasound transducers 102 that can be used to image and/or treat a region of interest. The transducer(s) 102 can be powered in such a manner as delivering both an ablative dose of focused ultrasound in a continuous or semi-continuous manner and/or a nonablative dose of focused ultrasound in a pulsed or continuous manner. Such a focused ultrasound (FUS) probe, capable of delivering ablative and nonablative treatment, can have many possible configurations, including:

1) A two-sided transducer that is flipped between a side with a crystal optimized for pFUS, generally designated 46, and a second side with a crystal optimized for aFUS (ablative focused ultrasound), generally designated 48 (FIG. 1a);
2) A single array transducer divided in at least two parts, one with crystals optimized for pFUS, generally designated 50, and one with crystals optimized for aFUS, generally designated 52 (FIGS. 1b and 1c); and
3) A single element or array transducer where the crystal(s) is driven at its fundamental frequency for pFUS and at its 3$^{rd}$ and/or 5$^{th}$ harmonic for aFUS.

The table below outlines some of the characteristics that differentiate the mechanism of action and the expected outcome of HIFU and pHIFU (pulsed high intensity focused ultrasound) (or pFUS).

| Parameter | HIFU | pHIFU (or pFUS) |
|---|---|---|
| Frequency | 1-4 MHz | 100 KHz-1 MHz |
| Temperature rise in C. | 30-50 | approximately 3-5 |
| Treatment Exposure Mode | Continuous | Pulsed |
| Beam On Time | 3-20 seconds | 1-10 m seconds |
| Focal site peak intensity (w/cm2) | 600-4000 | 100-1000 |
| Desired Cellular effect | Thermal coagulative necrosis | Mechanical Stress Hyperthermia |
| Cellular changes | Irreversible Cell death | Reversible Membrane and cellular changes |

Figure 6:
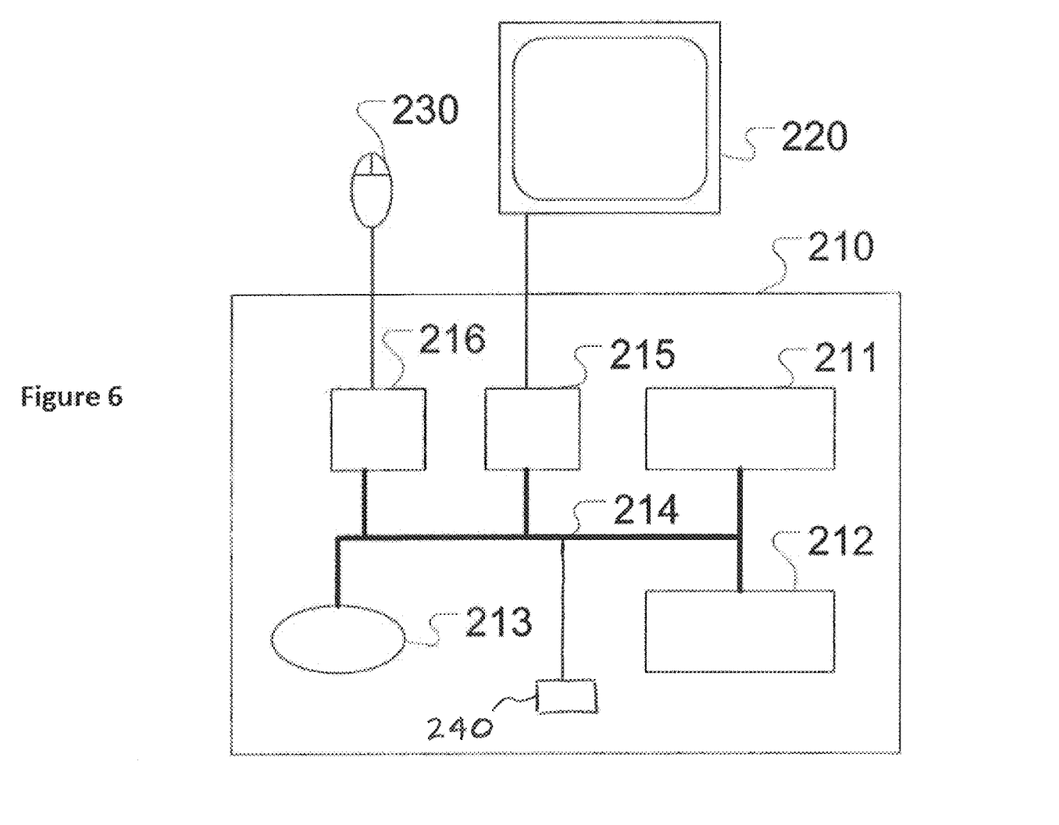
FIG. 6 is a schematic representation of an exemplary computing system useful for performing at least certain processes disclosed herein.

One or more of the above-described techniques and/or embodiments may be implemented with or involve software, for example modules executed on or more computing devices 210 (see FIG. 6). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power.

The storage device(s) 213 may be any type of non-transitory storage device (e.g., an optical storage device, a magnetic storage device, a solid state storage device, etc.). The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the display device 220 (e.g., in response to modules executed). The input controller(s) 216 may be operatively coupled (e.g., via a wired or wireless connection) to an input device 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 6 illustrates the computing device 210, the output device 220, and the input device 230 as separate devices for ease of identification only. However, the computing device 210, the display device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud services running on remote computing devices.

In one embodiment, the presently disclosed technology includes a method for delivering an ablative dose of focused ultrasound that will purposefully spare or not disrupt some portion of a volume of cancer cells targeted for ablation. The steps for doing so can include one or more of the below, in the below-listed or a modified order:

1. Segmenting or defining the target volume using a variety of imaging tools, including ultrasound (US), MRI, CT, and PET to identify the region targeted for treatment, which is subsequently defined using typical segmentation tools and algorithms resulting in a structure or structures that can be manipulated in a treatment planning system;
2. Inputting either the type of cancer, which generates the volume of tissue required for immunostimulation and/or stem cell homing or activation based on a nomogram, or inputting directly the volume of tissue required to receive a nonablative dose. In one embodiment, this input occurs into the computer system, which can store the probe properties, and be configured to determine the type of target tissue needed to accomplish the goal(s) described herein. This can occur during the treatment planning stages, for example, but generally after the cancer type is known (e.g., from imaging results, biopsy, etc.);
3. Determining, either automatically or manually, the thickness of the rim or area of targeted tissue or total volume of tissue required to be dosed sublethally;
4. Determining, either automatically or manually, the volume and/or location of tissue to be ablated, which is equal to the total target volume defined on the imaging study minus the region to treated with a nonablative dose;
5. Determining where the fall-off region of an ablative dose of focused ultrasound should fall such that the region to receive a nonablative dose of focused ultrasound actually receives a nonablative dose of focused ultrasound dose falloff projected to occur given the treatment parameters (e.g., diameter of dose, type of dose delivery, total dose, time to deliver dose, etc.); and/or
6. Delivering an ablative dose of focused ultrasound to the specified treatment volume thereby ablating the bulk of the targeted volume of cancer cells in the central portion of the tumor while exposing a rim of cancer cells to a sublethal dose of HIFU that will result in enhanced activation of an immune system response.

Alternatively, the regions targeted for ablation and nonablation can be treated using different focused ultrasound parameters delivered using a single or multiple ultrasound crystals. The steps for doing so can include one or more of the below, in the below-listed or a modified order:

For Both Embodiments (i.e., Immunostimulation and Stem Cell Homing/Activation):

1. Segmenting the target volume using a variety of imaging tools, including US, MRI, CT, and PET to identify the region targeted for treatment which is subsequently defined using typical segmentation tools and algorithms resulting in a structure or structures that can be manipulated in a treatment planning system;

For lmmunostimulation or Immune System Activation Embodiment:
2. Inputting either the type of cancer, which generates the volume of tissue required for immunostimulation based on a nomogram, or inputting directly the volume of tissue required to receive a nonablative dose;

For Stem Cell Homing and/or Activation Embodiment:
2. Inputting either the size of the anticipated tissue defect resulting from ablation that generates the volume of tissue required for stem cell homing and/or activation based on a nomogram, or inputting directly the volume of tissue required to receive a nonablative dose;

For Both Embodiments:
3. Determining, either automatically or manually, the thickness of the rim or area of targeted tissue or total volume of tissue required to be dosed sublethally;
4. Determining, either automatically or manually, the volume and location of tissue to be ablated which is equal to the total target volume defined on the imaging study minus the region to treated with a nonablative dose; and/or
5. Delivering to the region to be ablated an ablative dose of focused ultrasound using one set of focused ultrasound delivery parameters and characteristics and to the region to receive immunostimulation a nonablative dose of focused ultrasound using second set of focused ultrasound delivery parameters and characteristics, whereby the region designated to receive an ablative dose of focused ultrasound receives an ablative dose and the region required to receive a nonablative dose of focused ultrasound receives a nonablative dose of focused ultrasound, achieving the goal of ablating as much of the target volume as possible while delivering an immunostimulating dose of focused ultrasound to the volume of tissue required to produce an immunostimulatory response.

In one embodiment, the presently disclosed technology uses a first set of parameters to ablate cancer in a first region of a patient and second set of parameters to attract stem cells to a second, different region of the patient. Benefits of the presently disclosed technology directed to stem cell homing and/or activation are that it treats cancer and closes a tissue defect of the patient (i.e., heal and/or improve healing of damaged tissue). Optionally, one embodiment of the presently disclosed technology is targeted specifically at the rectum area of the patient because the act of ablation will create a tissue defect (e.g., one or more rectal fistulas) that could be problematic due to its anatomic function. The concept of the presently disclosed technology directed to stem cell homing can be applied to other targeted tissue and/or organs, such as the esophagus, colon, stomach and the like, for example, where a tissue defect from HIFU could result in serious side effects. Thus, optionally, the portions or organs of a patient that could benefit from the presently disclosed technology in which stem cell homing is provoked and/or activated include the rectum, colon, stomach, small bowel, gall bladder, uterus, vagina, bladder, oral mucosa, and skin.

In one embodiment, the volumes targeted by the presently disclosed technology directed to stem cell homing and/or activation share a common attribute: they themselves are a "vessel" that contain fluid (e.g., liquid and/or gas) that is not intended or beneficial to be released from the vessel from which they are held. Employing the presently disclosed technology directed to stem cell homing and/or activation can enhance sealing (e.g., healing) of a defect of a wall (i.e., of the vessel), such that the fluid(s) or contents of the vessel contained by tissue remain secure. This applies to each of the above-mentioned portions, organs, or tissues, except oral mucosa and skin. For these two target volumes, the tissue does not necessarily contain fluid or other material that is not supposed to be released per se, but the treatment (e.g., ablation) can create a defect in the container wall that can become problematic, e.g. infection or disfiguring, and therefore would benefit from earlier or quick closure.

The presently disclosed technology directed to stem cell homing and/or activation cannot necessarily be applied (or is not necessarily beneficial) to the destruction of tissue within other targeted organs, tissue, or glands, such as the prostate, breast, kidney or the like, where the target volume is contained within an organ or gland that is protected by a capsule that is not ablated. For example, for the prostate, tissue is ablated or destroyed within the prostatic capsule. The same applies to the liver or kidney, muscle, brain, breast, etc. With these portions, tissue, or organs, a hole is not created by ablation that might allow egress of toxic or potentially harmful or undesirable internal components that if move or escape might be dangerous or not ideal to the health of the patient (e.g., infection).

In one embodiment, stem cells are injected into or delivered to the patient. For example, the stem cells can be injected directly into or near the region, or can be introduced via a systemic injection, where stem cells are delivered to or near the region of interest by the vascular tree and retained in the region due to the beneficial homing aspects of pFUS or NAFUS. In one embodiment, the stems cells are injected intravenously or otherwise inserted into the patient. The nonablative dose of ultrasound (e.g., pFUS) causes the stem cells to home to the region of the patient that is being treated. In one embodiment, the stem cells circulate and are caused to exit the circulation and deposit or remain where the nonablative dose of ultrasound is localized.

The above-described stems cells are not endogenous to the region and are added by this injection or introduction. This is an area wherein immunotherapy and stem cell therapy differ. In immunotherapy, endogenous or exogenous immune system cells can be delivered to the patient. In stem cell therapy, such as the present embodiment, exogenous stem cells are delivered to the patient. Any form of stem cell (such as embryonic stem cells, various types of tissue-specific stems cells, mesenchymal stem cells, and/or induced pluripotent stem cells) that may be of therapeutic benefit to the repair of a tissue defect can be used. The form of stem cells can be selected based on indication. The introduction of stem cells to the relevant region can occur i) before ablation occurs, ii) after ablation and prior to the application of nonablative ultrasound, and/or iii) after both ablation and the application of nonablative ultrasound. Optionally, the introduction of stem cells can be in parallel with ablation or the nonablative dose of ultrasound.

Therefore, the presently disclosed technology is well adapted to attain the ends and advantages mentioned as well as those that are inherent therein. While numerous changes may be made by those skilled in the art, such changes are encompassed within the spirit of the presently disclosed technology as illustrated, in part, by the appended claims.

I claim:
1. A method of treating cancer, the method comprising the steps of:
   a) placing a high intensity focused ultrasound (HIFU) probe including at least one transducer proximate a designated treatment volume of a patient, the designated treatment volume being a macroscopic three-dimensional volume and including at least a portion of an organ, the designated treatment volume being located beneath subcutaneous fat of the patient;

b) ablating a first portion of the designated treatment volume with energy emanating from the transducer of the HIFU probe using a first set of parameters designed to achieve ablation of the first portion, this step including delivering HIFU via the HIFU probe at a frequency of at least 1 MHz for at least 3 seconds to raise a temperature of the first portion of the designated treatment volume to above 65° C., the first portion being a three-dimensional volume having a width, a height, and a depth, the first portion being located entirely beneath the subcutaneous fat of the patient such that ultrasound waves pass from the transducer through the subcutaneous fat so as not to treat the subcutaneous fat and the ultrasound waves coalesce at the first portion, the first portion not encompassing or contacting the organ;

c) delivering a nonablative dose of energy to a second portion of the designated treatment volume with energy emanating from the HIFU probe using a second set of parameters designed to achieve such a nonlethal dose, this step including use of a frequency between 100 KHz—1 MHz delivered in bursts between 1-10 milliseconds at a time, the second portion being a three-dimensional volume having a width, a height, and a depth, the second portion being located entirely beneath the subcutaneous fat of the patient and entirely encompassing the first portion such that an entire outer periphery of the first portion is contained within the second portion, the second portion having a larger width, height, and depth than the first portion and extending laterally beyond the first portion, the second portion encompassing or contacting the organ, the energy from the nonablative dose passing from the transducer through the subcutaneous fat so as not to treat the subcutaneous fat and the energy from the nonablative dose coalescing at the second portion; and d) injecting stem cells into the patient (i) after step b) and before step c), or (ii) after both step b) and step c), wherein the application of the nonablative dose of energy to the second portion provokes stem cell homing at the second portion, and wherein the provocation of stem cell homing encourages tissue regrowth to close one or more tissue defects.

2. The method of claim 1, wherein the probe is in a first position when the ablative energy is directed to the first portion, and wherein the probe is in the same first position during the application of the nonablative dose of energy to the second portion.

3. The method of claim 1, wherein the at least one transducer includes one or more ultrasound transducers configured to image and treat the designated treatment volume, the one or more ultrasound transducers including at least one first crystal optimized for pulsed focused ultrasound (pFUS) and at least one second crystal optimized for ablative focused ultrasound (aFUS), the at least one first crystal being located on a first side of the transducer and the at least one second crystal being located on an opposing second side of the transducer.

4. The method of claim 3, wherein the one or more ultrasound transducers are each single array transducers formed of a two parts, the two parts include at first crystal optimized for pFUS and a second crystal optimized for aFUS, and wherein the second crystal surrounds at least a portion of the first crystal.

5. The method of claim 1, further comprising:
defining the first portion of the designated treatment volume prior to ablating the first portion; and
defining the second portion of the designated treatment volume prior to ablating the first potion.

6. The method of claim 1, wherein step c) is delivered simultaneously to the step of ablating the first portion of the designated treatment volume.

7. The method of claim 6, wherein prior to placing the HIFU probe proximate the designated treatment volume, the method comprises imaging the designated treatment volume using at least one of ultrasound, magnetic resonance imaging, computed tomography and positron emission tomography.

8. The method of claim 7, wherein step d) occurs before step c).

9. The method of claim 1, wherein the stem cells are exogenous stem cells.

10. The method of claim 1, wherein the organ is an esophagus, rectum, stomach, colon, small bowel, gall bladder, uterus, vagina, bladder, oral mucosa, breast, prostate, liver, or kidney.

11. The method of claim 10, prior to step a), inputting the type of cancer to be treated into one or more computing devices, the one or more computing devices then generating the first set of parameters and the second set of parameters.

* * * * *